United States Patent [19]

Buysch et al.

[11] Patent Number: 5,310,849

[45] Date of Patent: May 10, 1994

[54] AMINO AND AMMONIUM ISOCYANATES, A PROCESS FOR THEIR PREPARATION, THEIR USE FOR THE PRODUCTION OF POLYMERS CONTAINING AMMONIUM GROUPS AND THE POLYMERS THUS PRODUCED

[75] Inventors: Hans-Josef Buysch, Krefeld; Klaus König, Odenthal; Alexander Klausener, Krefeld; Klaus Szablikowski, Walsrode; Jörn Breckwoldt, Rotenburg, all of Fed. Rep. of Germany

[73] Assignee: Wolff Walsrode AG, Walsrode, Fed. Rep. of Germany

[21] Appl. No.: 875,622

[22] Filed: Apr. 28, 1992

[30] Foreign Application Priority Data

May 1, 1991 [DE] Fed. Rep. of Germany ....... 4114221

[51] Int. Cl.$^5$ .............................................. C08G 18/70
[52] U.S. Cl. ......................................... 528/71; 528/44
[58] Field of Search ................................ 528/71, 44

[56] References Cited

U.S. PATENT DOCUMENTS 4,182,828  1/1980  Reischi et al. ..................... 528/71

FOREIGN PATENT DOCUMENTS 631961   5/1963  Belgium .
0001603  5/1979  European Pat. Off. .
0131859  1/1985  European Pat. Off. .
890519   2/1962  United Kingdom .

OTHER PUBLICATIONS

Chemical Abstracts, vol. 80, 1974, p. 394.

Primary Examiner—John Kight, III
Assistant Examiner—Duc Truong
Attorney, Agent, or Firm—Sprung Horn Kramer & Woods

[57] ABSTRACT

The present invention relates to new amino and ammonium isocyanates, to a process for their preparation, e.g. by the reaction of certain ureas with isocyanates, and to the use of the new substances for the production of polymers containing ammonium groups.

6 Claims, No Drawings

AMINO AND AMMONIUM ISOCYANATES, A PROCESS FOR THEIR PREPARATION, THEIR USE FOR THE PRODUCTION OF POLYMERS CONTAINING AMMONIUM GROUPS AND THE POLYMERS THUS PRODUCED

The present invention relates to new amino and ammonium isocyanates corresponding to Formula I $$Y-R-NCO \quad (I)$$

wherein
R denotes a $C_2$-$C_{10}$-alkylene group,
Y denotes an amino group corresponding to the formula

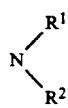

or an ammonium group corresponding to the formula

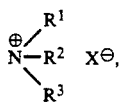

$R^1$, $R^2$ and $R^3$ are identical or different and denote $C_1$-$C_5$-alkyl or $R^1$ and $R^2$ together with the N atom denote a 5-membered or 6-membered ring optionally containing an O-atom,
$R^3$ may in addition denote allyl, methallyl or benzyl, and
$X^\ominus$ denotes an anion of a strong acid,
to a process for their preparation by the reaction of ureas corresponding to Formula II

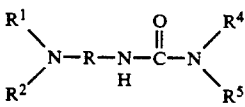

wherein $R^4$ and $R^5$ are identical or different and denote $C_{1-5}$-alkyl or $R^4$ and $R^5$ together with the N-atom stand for a 5-membered or 6-membered carbocyclic ring optionally interrupted by an oxygen atom with mono- or polyisocyanates at temperatures of from 50° to 250° C. and pressures of from 0.001 to 1 bar and distillative removal of the aminoisocyanates corresponding to Formula III

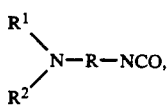

to their alkylation with compounds corresponding to formula $R^3X$ to form the ammonium isocyanates corresponding to Formula IV

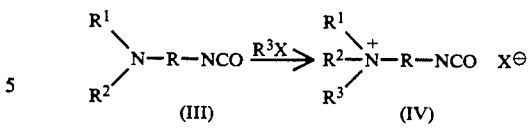

and lastly, to the formation of polymers containing ammonium groups by the reaction of polymers containing OH groups with the isocyanates corresponding to Formula IV.

It is known to decompose ureas of lower amines by heat in the presence of high boiling isocyanates in low boiling isocyanates and to remove the low boiling isocyanate from the reaction mixture. The reaction proceeds according to the following scheme:

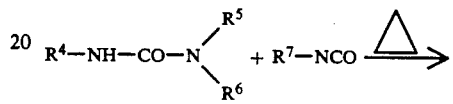

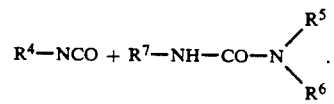

This reaction is described in detail in EP-A 001 603.

It has now surprisingly been found that this method may also be used for obtaining isocyanates containing tertiary amino groups. This is all the more surprising in view of the fact that tertiary amines catalyse the oligomerisation of isocyanates, for example to form isocyanurates, in particular at elevated temperatures. At the present high amine concentration and high decomposition temperature, therefore, one would expect rapid and complete conversion of the new aminoisocyanates into relatively high molecular weight products.

The invention further relates to a process for the preparation of amino and ammonium isocyanates, characterised in that the process is carried out in the following stages:

a) Reaction of carbonic acid derivatives with primary-tertiary diamines corresponding to Formula IIa with the formation of a urethane derivative.

Suitable starting materials for the process according to the invention are: Primary-tertiary diamines corresponding to Formula IIa wherein R denotes a $C_2$-$C_{10}$-alkylene group which may be linear or branched, preferably $C_2$ to $C_8$-alkylene, most preferably $C_2$ to $C_6$-alkylene; $R^1$ and $R^2$ denote $C_1$ to $C_5$-alkyl or together with the N atom they denote a 5-membered or 6-membered ring optionally containing an oxygen atom, preferably $C_1$-$C_4$-alkyl, $-(CH_2)_4$, $-(CH_2)_5$ or $-(CH_2CH_2)_2O$, most preferably $CH_3$, $C_2H_5$, $(CH_2)_4$ $(CH_2)_5$ and $-(CH_2CH_2)_2O$.

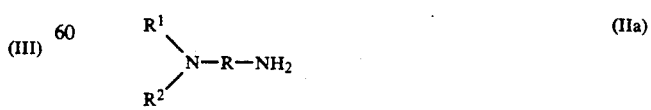

The following are examples:

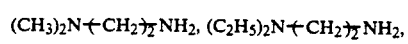

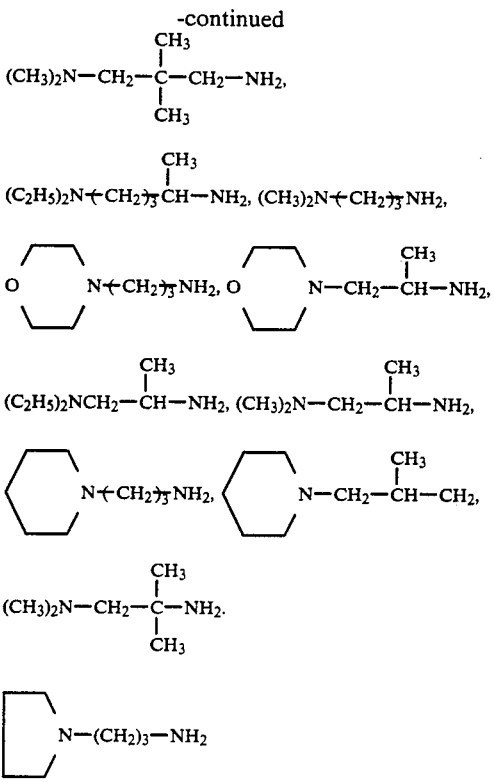

Reaction of the urethane derivative with secondary amines corresponding to the formula

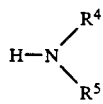

to form the urea derivative corresponding to Formula II in which the substituents $R^4$ and $R^5$ have the meaning indicated above.

c) Thermal decomposition of the ureas in the presence of high boiling isocyanates with removal of the aminoisocyanates of Formula III by distillation.

Suitable starting isocyanates are described in detail in EP-A 001 603 as are also the procedures on pages 5 to 8. In the present case, however, it is not necessary to carry out the process in the presence of carbodiimides. The aliphatic isocyanates mentioned are particularly preferred for the preparation of the aminoisocyanates according to the invention.

The aminoisocyanates of Formula III obtained by these means are converted into quaternary compounds with alkylating agents of the formula $R^3X$ by introducing the aminoisocyanate into the alkylating agent or conversely introducing the alkylating agent into the aminoisocyanate or introducing both into the reaction vessel at the same time. The reaction may be carried out solvent-free or in suitable inert solvents. Examples of suitable solvents include hydrocarbons such as hexane, pentane, cyclohexane, benzene, toluene or xylene, halogenated hydrocarbons such as dichloromethane, trichloromethane, dichloroethane, trichloroethane, chlorobenzene, bromobenzene or dichlorobenzene, ethers such as diethyl or diisopropylether, anisole, dibutylethers and nitriles such as acetonitrile, propionitrile and benzonitrile. The alkylating agent may also be used as diluent if it can be recovered easily, e.g. methyl chloride, ethyl chloride, methyl iodide or propylbromide. The reaction is carried out at 0° to 100° C., preferably at 10° to 80° C.

Suitable alkylating agents $R^3X$ are those in which $R^3$ stands for $C_1$-$C_5$-alkyl, allyl, methallyl or benzyl, preferably $C_1$-$C_4$-alkyl, allyl and benzyl, most preferably methyl, ethyl, allyl and benzyl. X is the residue of a strong acid, i.e. an acid having a $pk_a$ of less than 3 measured in water, preferably less than 2. Examples include hydrohalic acids such as HCl, HBr and HI, sulphuric acid, phosphoric acid, sulphonic acids such as benzene, chlorobenzene and toluene sulphonic acid and phosphonic acids such as chlorobenzene and cyanobenzene phosphonic acid.

The ammonium isocyanates prepared by this method are novel and therefore a subject of the present invention. They are valuable starting materials for the production of polymers containing quaternary ammonium groups, which are obtained by reacting OH-containing polymers with these ammonium isocyanates in solution or suspension.

The following are examples of suitable OH group-containing polymers: Polyvinyl alcohols, polyacrylates which have been prepared from monomers containing OH groups, such as $\beta$-hydroxyethyl(meth)acrylate, and especially polysaccharides, starches, dextrins, glycogen and polyglucosans such as cellulose and its derivatives, e.g. methyl cellulose, hydroxyethyl cellulose, hydroxypropyl cellulose, mixed cellulose ethers such as methylhydroxyethyl cellulose, methylhydroxypropyl cellulose, hydroxyethyl hydroxypropyl cellulose, sulphoethyl cellulose, sulphoethylcarboxymethyl cellulose, methylsulphoethyl cellulose, hydroxyethylsulphoethyl cellulose, dihydroxypropyl cellulose, dihydroxypropyl hydroxyethyl cellulose, dihydroxypropyl carboxymethyl cellulose, carboxymethyl cellulose, esters and salts thereof with sodium, potassium, calcium or ammonium ions, carboxymethyl hydroxyethyl cellulose, cellulose sulphate, polyfructosans such as inulin and graninin, polymannosans, polygalactosans and mixed polysaccharides such as hemicelluloses as well as polyxylosans, polyarabiosans and heteropolysaccharides such as gellan, xanthane and pullulan.

Celluloses and their derivatives, starches and dextrins are preferred, and cellulose, methyl cellulose, hydroxyethyl cellulose, hydroxypropyl cellulose and starch are particularly preferred.

Cationic polymers containing quaternary ammonium groups, especially cationic polysaccharides, are important products and auxiliary agents for the manufacture of paper, medical filters, cosmetic cleaning agents and flocculating agents for clarifying effluent.

The preparation of such products has not hitherto been solved satisfactorily. Several processes have been proposed but they generally only lead to low degrees of substitution on the polysaccharides. Highly substituted polysaccharides may, however, be obtained according to EP-A 367 003 (see also the literature cited there). The process described there, however, requires three successive polymer analogous reactions on the polysaccharide and therefore entails a corresponding expenditure in time and labour.

It has now been found that the ammonium isocyanates described above can very easily be reacted with polysaccharides and give rise in a single polymer analogous reaction step to cationic polysaccharides which are comparable to those described in EP-A 367 003. The use of the isocyanates according to the invention corresponding to Formula I for the production of cationic polymers, especially cationic polysaccharides, and the cationic polymers produced by this process, especially cationic polysaccharides, are therefore also subject matters of the present invention.

The reaction of the ammonium isocyanates IV with the OH group-containing polymers is carried out in solution or dispersion, the polysaccharides being preferably used as suspensions because they form very highly viscous solutions which can only be obtained with low solids contents and therefore require a large reaction space and complicated methods of working up.

Suitable solvents and dispersing agents are inert under the reaction conditions. Examples include hydrocarbons such as cyclohexane, pentane, heptane, isooctane, benzene and toluene, halogenated hydrocarbons such as methylene chloride, chloroform, dichloroethane and trichloroethylene, ethers such as diethyl, diisopropyl and dibutylether, dioxane, anisole, dimethoxyethane, esters such as ethyl acetate and butyl acetate, ethyl propionate and ethyl benzoate, ketones such as acetone, methyl ethyl ketone, diethyl ketone, methyl isopropyl ketone, cyclohexanone and acetophenone, amides such as dimethylformamide and dimethylacetamide, tetramethylurea, N,N-dimethyl-ethyleneurea, N-methylpyrrolidone, N-methylcaprolactam, nitriles such as acetonitrile, propionitrile, benzonitrile and β-methoxypropionitrile and β-cyano-β'-methoxy-diethylether.

The reaction temperature is at 0° to 120° C., preferably at 10° to 100° C., most preferably at 15° to 80° C.

The starting materials and solvents or dispersing agents should be substantially anhydrous to prevent side reactions of the ammonium isocyanate with water as far as possible.

The OH group-containing polymer is generally introduced into the reaction vessel in the required medium, and the ammonium isocyanate is added as such or dissolved in the solvent in which the alkylation also took place. One and the same medium may be used for the alkylation and for the polymer analogous reaction. The reaction time is from 30 minutes to several hours.

The isocyanate addition to the OH-functional polymers generally proceeds slowly and is therefore preferably catalysed. The catalysts are those conventionally used for the formation of urethanes from isocyanates and alcohols and are introduced in the proposed quantities (see Houben-Weyl, Volume E20, 1604 et seq (1987)). Organic tin compounds such as dibutyl tin dilaurate or tin laurate are particularly preferred catalysts.

The invention will now be illustrated in more detail with the aid of the following Examples in which percentages are percentages by weight unless otherwise indicated.

EXAMPLE 1

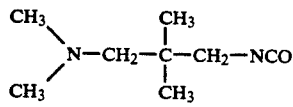

381 g (1.78 mol) of diphenylcarbonate are made up into a slurry with 200 ml of 1,2-dichloroethane and 232 g (1.78 mol) of dimethylaminoneopentylamine are added dropwise at 0° to 10° C. with ice cooling (time 60 minutes). The reaction to the O-phenylurethane is completed after 2 hours at 20° C. (titration with HCl). 130 g (1.78 mol) of diethylamine are then added dropwise while the reaction mixture is cooled with cold water and the mixture is then briefly heated to 100° C. until the urethane has been completely converted into the trisubstituted urea.

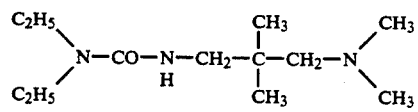

Dichloroethane followed by phenol is then distilled off, first at 200 mm and finally at 1 mm, 450 g of hexamethylene diisocyanate (2.68 mol) are added to the liquid residue at 60° C. and the reaction mixture is heated up at 15 mbar. Distillation begins at a sump temperature of 100° C. and continues to 150° C. 245 g (88.4% of the theoretical) of the title compound are obtained in 2 hours at b.p.$_{15}$ 70° C. in the form of a mobile, water-clear, malodorous liquid.

EXAMPLE 2

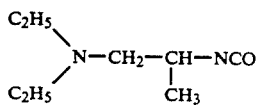

The starting amine was converted analogously to Example 1 into methylene chloride by means of diphenylcarbonate and then into the urea by means of diethylamine and lastly into the title compound by means of hexamethylene diisocyanate.

Yield: 85% of the theoretical, b.p. 30° C. at 0.4 mbar, 72° C. at 13 mbar, 99% according to gas chromatographic analysis.

EXAMPLE 3

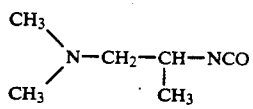

This compound is prepared analogously to Example 1 but using isophorone diisocyanate instead of hexamethylene diisocyanate.

Yield: 40%, bp. 70° C./50 mbar;
m.p. 59° C.; NCO: 98.5% of theoretical.

EXAMPLE 4

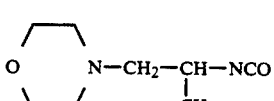

Preparation analogous to Example 3
Yield: 75%, b.p. 50° C. at 0.5 mbar, 99.3% according to gas chromatographic analysis.

EXAMPLE 5

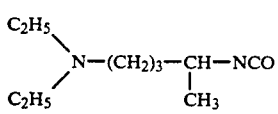

Preparation analogous to Example 3.
Yield: 82% of theoretical, b.p. 48° C. at 0.3 mbar, 100% according to gas chromatographic analysis.

EXAMPLE 6

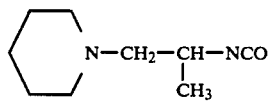

Preparation analogous to Example 3.
Yield: 79% of theoretical, b.p. 42° C. at 0.4 mbar, 99% according to gas chromatographic analysis.

EXAMPLE 7

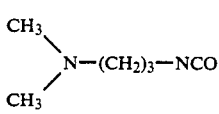

Preparation according to Example 3.
Yield: 71% of theoretical, bp. 57° C. at 13 mbar, 99.8% according to gas chromatographic analysis.

EXAMPLE 8

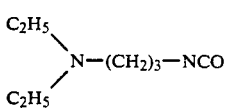

Preparation analogous to Example 3.
Yield: 79% of theoretical, b.p. 26° C. at 0.2 mbar, 98% according to gas chromatographic analysis.

EXAMPLE 9

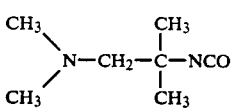

Preparation according to Example 3.
Yield: 50% of theoretical, b.p. 47° C. at 13 mbar.

EXAMPLE 10

128 g (1.0 mol) of the distillate from Example 7 are dissolved in 200 ml of anhydrous methylene chloride and added dropwise within one hour to an anhydrous boiling solution of 130 g (1.02 mol) of dimethylsulphate in 300 ml of methylene chloride. The reaction mixture is then kept under reflux for 1 hour. After removal of methylene chloride by distillation under vacuum, a yellowish oil is obtained which according to analysis corresponds to the following formula:

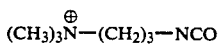

Other ammonium isocyanates are obtained by this method from the aminoisocyanates of Examples 2 to 9.

EXAMPLE 11

90 g (0.51 mol with respect to the methyl cellulose unit) of methyl cellulose having a degree of substitution DS of 1 (DS=number of substituents per cellulose unit) are suspended in 1000 ml of anhydrous methylene chloride and dehydrated by azeotropic distillation. An easily stirrable suspension in about 500 ml of methylene chloride is obtained. 40 g of anhydrous dimethylacetamide, 0.1 g of dibutyl tin dilaurate and ¾ of the reaction product from Example 10, corresponding to 0.75 mol of ammonium isocyanate, are added to this suspension. The mixture is boiled under reflux and the progress of isocyanate addition is determined on samples. The reaction is stopped after 20 hours and the reacted cellulose is suction filtered, thoroughly washed three times with methylene chloride and four times with isopropanol and dried under a vacuum at 50° C. 215 g of a cationic cellulose which shows a strong urethane band at 1725 cm$^{-1}$ in the IR spectrum and has an N-content of 7.8% and an S-content of 9.7% are obtained. This corresponds to a degree of substitution DS of about 1.3.

We claim:

1. Amino and ammonium isocyanates corresponding to the general formula I

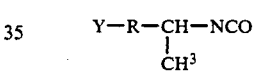

or formula (Ia)

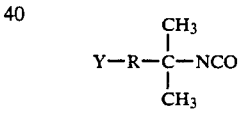

wherein
R denotes an alkylene group wherein the number of carbon atoms between Y and —NCO is 2 to 10,
Y denotes an amino group of the formula

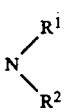

an ammonium group of the formula

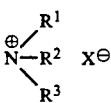

$R^1$, $R^2$ and $R^3$ are identical or different and denote alkyl groups having 1 to 5 carbon atoms or
$R^1$ and $R^2$ together with the N atom optionally denote $(CH_2)_4$, $(CH_2)_5$ or $(CH_2CH_2)_2O$,
$R^3$ optionally denotes allyl, methallyl or benzyl, and
$X^\ominus$ denotes an anion of a strong acid.

2. A process for the preparation of aminoisocyanates according to claim 1 corresponding to Formula III

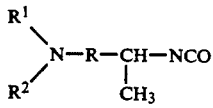
(I)

or formula (IIIa)

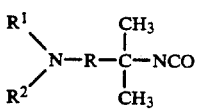
(IIIa)

by the reaction of ureas with isocyanates followed by thermal decomposition, characterised in that the ureas used correspond to Formula II

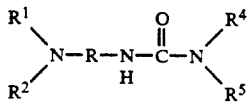
(II)

wherein $R^4$ and $R^5$ have the meaning of $R^1$ and $R^2$.

3. An isocyanate according to claim 1, wherein Y is an ammonium group of the formula

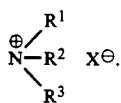

4. In the production of polymers containing quaternary ammonium groups by reacting an OH-containing polymer with a substituted ammonium isocyanate, the improvement which comprises employing as the substituted ammonium isocyanate an ammonium isocyanate according to claim 3.

5. A cationic polymer produced by the process of claim 4.

6. A process for the preparation of aminoisocyanates according to claim 1 corresponding to Formula IV

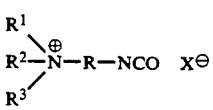
IV comprising alkylating an aminoisocyanate corresponding to Formula III

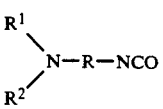
(III)

with a compound of the formula $R^3X$ wherein R, $R^1$, $R^2$ and $R^3$ have the meanings indicated in claim 1.

* * * * *

UNITED STATES PATENT AND TRADEMARK OFFICE
CERTIFICATE OF CORRECTION

PATENT NO. : 5,310,849

DATED : May 10, 1994

INVENTOR(S) : Hans-Josef Buysch, et al.

It is certified that error appears in the above-identified patent and that said Letters Patent is hereby corrected as shown below:

Col.8, Line 68            Delete "$X^{\oplus}$" and substitute --$X^{\ominus}$--

Signed and Sealed this

Seventh Day of December, 1999

Attest:

Q. TODD DICKINSON

*Attesting Officer*      *Acting Commissioner of Patents and Trademarks*